United States Patent [19]
Montoya et al.

[11] Patent Number: 5,342,182
[45] Date of Patent: Aug. 30, 1994

[54] SELF REGULATING BLOOD PUMP WITH CONTROLLED SUCTION

[75] Inventors: Jean P. Montoya; Scott I. Merz; Robert H. Bartlett, all of Ann Arbor, Mich.

[73] Assignees: The Regents of the University of Michigan; Constitutional Corporation of the State of Michigan, Ann Arbor, Mich.

[21] Appl. No.: 161,128

[22] Filed: Dec. 2, 1993

Related U.S. Application Data

[60] Division of Ser. No. 926,961, Aug. 7, 1992, Pat. No. 5,281,112, which is a continuation-in-part of Ser. No. 841,349, Feb. 25, 1992, Pat. No. 5,222,880.

[51] Int. Cl.⁵ .................. F04B 43/08; F16L 11/08
[52] U.S. Cl. .................. 417/477 R; 417/474; 138/119; 138/128
[58] Field of Search .............. 417/474, 475, 476, 477, 417/478, 479; 138/157, 119, 128; 251/4, 6, 7

[56] References Cited

U.S. PATENT DOCUMENTS

| | | | |
|---|---|---|---|
| Re. 25,788 | 6/1965 | Sheridan | 604/283 |
| 3,046,903 | 7/1962 | Jones | 417/435 |
| 3,175,498 | 3/1965 | Romrer | 417/474 |
| 3,295,556 | 1/1967 | Gertsma | 138/119 |
| 3,781,142 | 12/1973 | Zweig | 417/477 |
| 3,816,035 | 6/1974 | Malbel | 417/477 |
| 4,031,745 | 6/1977 | McCarty | 72/367 |
| 4,275,761 | 6/1981 | Waldhauser | 137/595 |
| 4,478,661 | 10/1984 | Lewis | 156/92 |
| 4,515,589 | 5/1985 | Austin et al. | 604/122 |
| 4,540,350 | 9/1985 | Strficher | 417/475 |
| 4,650,471 | 3/1987 | Tamari | 604/153 |
| 4,767,289 | 8/1988 | Parrot | 417/477 |
| 4,954,055 | 9/1990 | Raible et al. | 417/477 |

Primary Examiner—Richard A. Bertsch
Assistant Examiner—Peter Korytnyk
Attorney, Agent, or Firm—Harness, Dickey & Pierce

[57] ABSTRACT

A peristaltic pump having controlled suction. In one embodiment, the pump includes a tubing which is collapsed when the internal pressure of the tubing is equal to or less than ambient. In this state, the pump is unable to generate negative pressures. An air-tight housing may be provided over the tubing and connected to a vacuum source. Upon a vacuum being applied, the tubing is capable of controllably producing negative pressures, allowing the pump to be operated as a suction pump. In another embodiment the tubing exhibits a variable cross-sectional width.

16 Claims, 5 Drawing Sheets

SELF REGULATING BLOOD PUMP WITH CONTROLLED SUCTION

STATEMENT OF GOVERNMENTAL SUPPORT

This invention was made with support from the U.S. Government under Grant No. 5 R01 HD15434 awarded by the National Institute of Health. The U.S. Government has certain rights in this invention.

CROSS REFERENCE TO RELATED APPLICATION

This is a division of U.S. patent application Ser. No. 07/926,961, filed Aug. 7, 1992, now U.S. Pat. No. 5,281,312 which is a continuation-in-part of application Ser. No. 841,349, filed Feb. 25, 1992, now U.S. Pat. No. 5,222,880.

BACKGROUND AND SUMMARY OF THE INVENTION

The present invention relates to pumps and particularly to peristaltic pumps in which a fluid is forced through a tube by progressively compressing the tube at spaced apart intervals. Pumps of this general type have found particular utility in the medical field for transferring blood and other fluids between a patient and an extracorporeal device.

While a variety of pumps have been previously used, pumps used in connection with extracorporeal circulation are most commonly of the peristaltic type. Medical procedures which commonly employ peristaltic pumps include open heart surgery for circulating blood between a patient and a heart lung machine, dialysis procedures for transferring blood between a patient and a dialyzer, bypass surgery to remove blood from the open thoracic cavity, and continuous care situations for the pumping of intravenous solutions.

Peristaltic pumps are volumetric pumps in which a linearly moving or rotating member progressively compresses a flexible tube at spaced apart intervals to propel a fluid through the tube. A principal advantage of the peristaltic pump is its simplicity of operation and the absence of contact between the fluid, such as blood, and frictional surfaces, such as internal valves, which can be responsible for a variety of hazards. Instead of directly contacting the rotating member of the pump, the fluid is passed through a chemically inert tube.

Pumps of this type exhibit certain disadvantages which are inherent in the pumps themselves. Current roller pumps, often used for pumping blood, are typically driven by a constant speed motor which draws blood at a substantially constant rate. If a line downstream of the pump becomes occluded, the pump can over pressurize and rupture the downstream vessel. If a line upstream of the pump becomes occluded, the pump can generate dangerously low negative pressures, hemolyze the blood, and empty the tissue vessel of the patient causing a collapse of the vessel and resulting in damage to the tissue at the drainage catheter tip. Roller pumps in general are also inefficient in their operation. Much of the energy which is consumed by the pump is used to deform the thick walls of the flexible tubing, an action which in and of itself does not contribute to output flow. Furthermore, during long term use with a patient, the tubing presently employed with standard roller pumps requires being "walked" or replaced because of the wear induced by the cyclic application of high bending stresses as the rollers occlude the tube.

Pumps can be found in the prior art with regulating devices to control the available pumping volume of the pump. For example, in one peristaltic pump, described in U.S. Pat. No. 3,784,323, the material and thickness of the tube is selected so that there is a predetermined differential pressure between the exterior and interior of the tube. Collapse of the tube wall, limiting the flow rate of blood through the tube, occurs as a function of the pump inlet pressure. Thus, the flow rate through the pump will lessen and the tube will become restricted if the supply of blood decreases. This prevents a collapse of the tissue vessel and possible damage thereto. However, the restricted tubing is only partially collapsed and allows the pump to produce very high negative pressures. Furthermore, when in its collapsed state, high bending stress are induced in the crimped edges of the tubing resulting in a limited useful life.

In another peristaltic pump as described in U.S. Pat. No. 4,515,589, the pump is provided with a pumping element comprised of an outer tubing and an inner tubing. An annular air space, maintained between the inner and outer tubing, is vented to atmosphere. When the hydrostatic head of a blood reservoir is maintained above a given pump head level, the inner tubing will expand and fill with blood. When the reservoir level of blood drops below the pump head level, the inner tube collapses and the pump output stops. However, on "full" collapse of the inner tubing, two passageways remain open as the cross-section of the inner tube assumes a dumbbell or ∞ (infinity symbol) configuration. The inner tube is therefore not "completely" collapsed. Also, the inner tubing repeatedly experiences high bending stresses at its edges as it becomes occluded, both during forced collapse caused by the rollers and during collapse as a result of a loss of pressure, which leads to fatigue and wear in the tubing.

With the above described prior art in mind, it is an object of this invention to provide for an improved peristaltic pump having inherent pressure regulation and in which, the output flow is dependent upon the inlet supply. A peristaltic pump according to this invention exhibits low hemolysis and does not generate negative pressures.

Another object of this invention is to provide for a peristaltic pump having inherent pressure regulation while also being capable of exhibiting controllable suction when desired.

A further object of this invention is to provide for a peristaltic pump which exhibits an increased pumping efficiency and which has increased durability permitting use in long term support situations.

In achieving the above objects, the present invention utilizes a combination of features and provides for a peristaltic pump in which a flexible tubing is acted upon by rollers which progressively compress the tubing at spaced apart locations. The tubing itself is of a shape which is naturally flat and occluded when the pressure within the tubing is equal to or less than ambient pressures. The tubing is positioned in the peristaltic pump such that a flat side of the occluded tube is laid flat along the width of the rollers with the edges of the tubing away from the center of the rollers. An air-tight housing connected to a vacuum source encloses the peristaltic pump and allows for control of the pressure within the housing.

As the rollers are rotated, a peristaltic motion is imparted to the tubing. This motion in turn drives the blood from the inlet of the pump to its outlet. During operation, blood is supplied to the inlet at a pressure above ambient, the tubing fills and inflates, and the progressive compression of the tubing produces the pumping action. With the internal pressure of the housing at ambient, if the supply of blood to the pump is discontinued, blood will be pumped out of the tubing as the tubing completely flattens back into its natural or free condition. Being completely flat and occluded when no blood is being supplied to the pump, no negative pressures are generated within the tubing by the rollers.

If a slight vacuum is applied to the housing, thereby biasing the tubing into an unoccluded state, a suction equal to the vacuum will be produced as the rollers are rotated over the tubing. Thus, the pump can be used as a suction pump during operation.

Additionally, the novel shape of the tubing in the present invention allows the tubing to assume its completely occluded position without inducing high bending stresses along the edges of the tubing. This design therefore minimizes wear and fatigue and increases the durability of the tubing enabling and enhancing use in long term use situations.

As an alternative to the completely occluded tubing and vacuum housing mentioned above, when it is desirable to operate the pump as a suction pump, a slight and controllable suction can be generated within the tubing by employing a resilient tubing which is mildly biased into an unoccluded free cross-sectional shape. In this version, the tubing is provided with a mild unoccluded bias so that when a given pressure, less than ambient, is generated within the tubing, the tubing will collapse into its completely occluded or flat condition. The complete collapse of the tubing at a low negative pressure prevents higher hazardous negative pressures from being generated within the tubing.

The tubing can also be provided with a variable cross-sectional width. A variable cross-section tubing can allow for minimizing of the total pump priming volume and can allow for higher withheld pressures between the rollers at lower tensions of the tubing.

The peristaltic pump of the present invention also includes a mechanism for controlling the positive pressure which can be generated within the tubing. In this regard, the pump is provided with a mechanism which varies the tension of the tubing. The tensioning mechanism simultaneously adjusts the positions of both the inlet and outlet ends of the tubing. This reduces the distance which has previously required, in re-positioning the inlet or outlet alone, for the same amount of tension adjustment. The tensioning mechanism also "absorbs" or counters displacement of the tubing caused by the changing position of the rollers and thus allows for a flexible but inelastic tubing to be used.

One embodiment of a generally inelastic tubing is disclosed. In the embodiment, the tubing is reinforced with a fabric mesh that substantially prevents elongation of the tubing under tension.

An adjustable occlusion block is provided with the pump to permit accurate control of the outlet pressure as a roller disengages from the tubing adjacent to the outlet of the pump.

Additional benefits and advantages of the present invention will become apparent to those skilled in the art to which this invention relates from the subsequent description of the preferred embodiments and the appended claims taken in conjunction with the accompanying drawings.

DETAILED DESCRIPTION OF THE PREFERRED EMBODIMENTS

Figure 1:
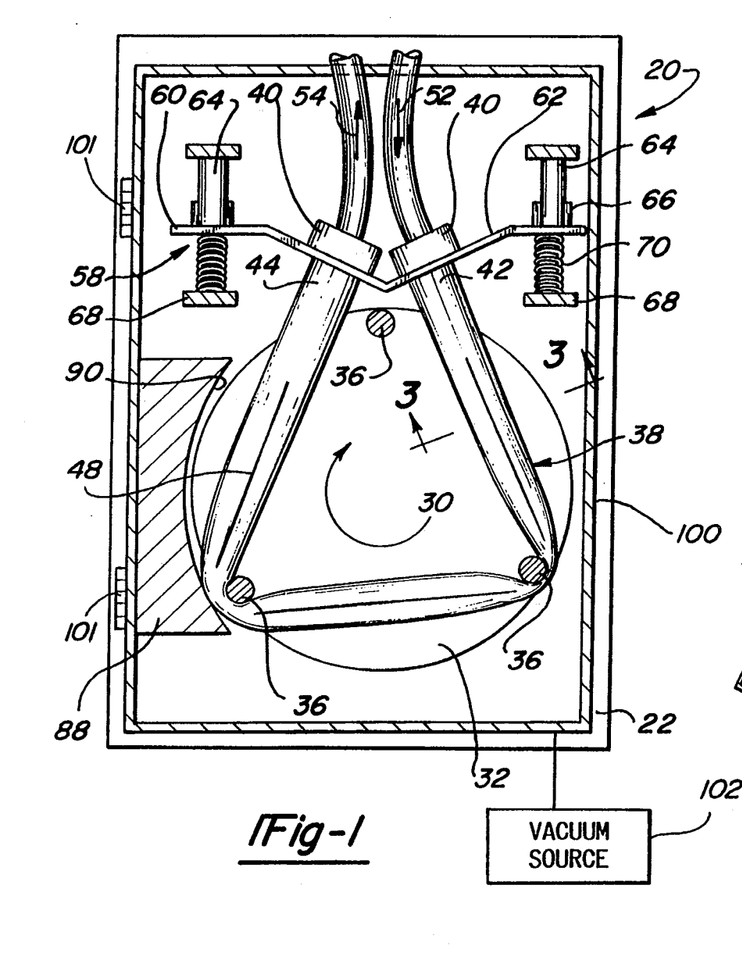
FIG. 1 is a front elevational view of a peristaltic pump incorporating the principals of the present invention.

Now with reference to the drawing, a peristaltic pump used for pumping fluid, such as blood, from a patient to an extracorporeal device (not shown) and back to the patient, is illustrated in FIG. 1 and generally designated at 20. It is anticipated that the pump 20 of the present invention will have utility in a variety of extracorporeal applications including, but not limited to, cardiopulmonary bypass, blood oxygenation, carbon dioxide removal, hemodialysis, blood filtration and other medical procedures. As will be more fully understood from the discussion which follows, the pump 20 can alternately be used as a positive pressure pump or a suction pump. One example of when the pump 20 would be used as a suction pump is during bypass surgery where the pump 20 is used exclusively to withdraw or "suck up" free blood from the open thoracic cavity.

Generally, the pump 20 is comprised of a frame 22 which includes a wheel or rotor 24. The rotor 24 is mounted to the frame 22 for rotation about an axis defined by a shaft 26 centrally disposed therein. The shaft 26 is driven by an electric motor or other suitable driving means which causes the rotor 24 to rotate, indicated as being clockwise by arrow 30 in FIG. 1.

The rotor 24 itself includes a pair of plates, hereinafter designated as the interior plate 32 and the exterior plate 34, between which are mounted a plurality of rollers 36. (For the sake of clarity in describing the underlying structures, the pump 20 is illustrated in FIG. 1 with the exterior plate 34 removed.) The rollers 36 are axially aligned with the shaft 26 and are radially displaced around the rotor 24 at equal distances. In this manner, as the rotor 24 is rotated by the motor 28, the rollers 36 will move in a circular path. In the illustrated embodiment, three rollers 36 are shown as being spaced approximately 120° apart. As the skilled artisan will appreciate, the number of rollers utilized will depend on the specific application and the rotor 24 can be designed to carry the rollers 36 in a non-circular path.

Each roller 36 is mounted in the rotor 24 so as to be rotatable about an axis extending therethrough parallel to the shaft 26. For reasons more fully described below, the rotational mounting allows the rollers 36 to move along a flexible conduit or tubing 38 without a significant amount of frictional pull on the tubing 38.

The flexible tubing 38 is positioned around the array of rollers 36 and secured by an attachment means, generally designated at 40 and further described below, which secures both an inlet end 42 and an outlet end 44 of the flexible tubing 38. The tubing 38 forms the pumping chamber of the pump 20.

A housing 100 is mounted to the frame 22 and protectively encloses the tubing 38, the rotor 32, and a tensioning mechanism 58 which is further discussed below. The housing 100 forms an air-tight chamber with the frame 22 and is coupled to a vacuum source 102 of a variety known to the industry. To provide access to the various components of the pump 20, the housing 100 may be hinged 101 to the frame 22 or provided with a hinged and sealable door or panel. As will be more fully understood from the discussion which follows, the pump 20 of the present invention can be alternately operated so that (1) no negative pressures are produced internally of the tubing 38 or (2) low or negative pressures are produced internally of the tubing 38 enabling suction to be performed. As used herein, negative pressures are defined as being subatmospheric pressures.

Figure 4:
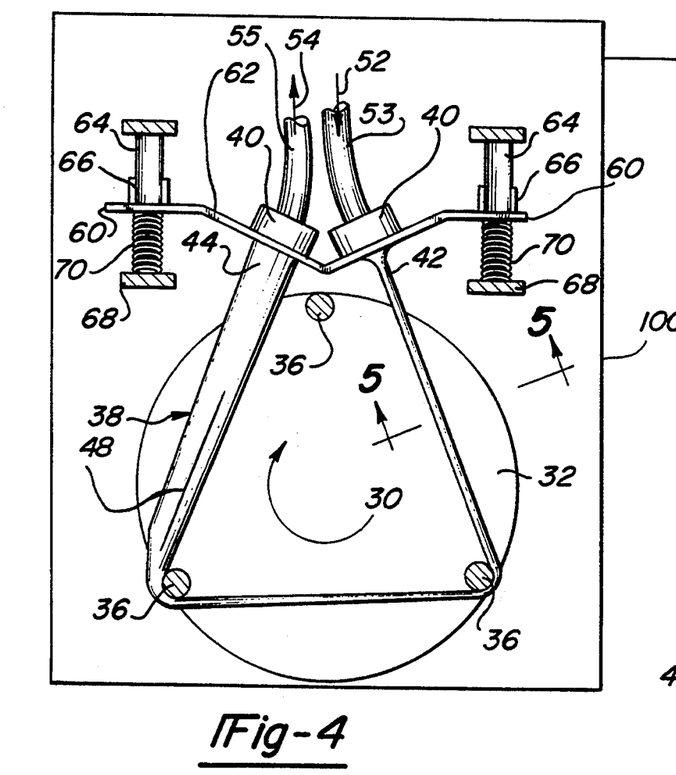
FIG. 4 is a simplified front view of a peristaltic pump incorporating the principles of the present invention when the supply of pumping fluid has been discontinued.
Figure 5:
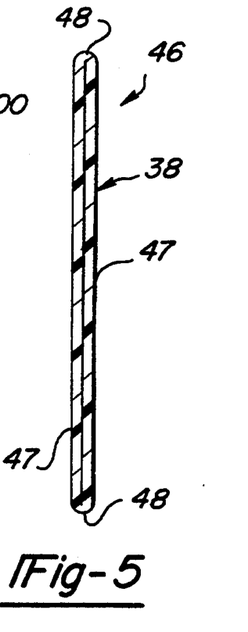
FIG. 5 is a cross-sectional view taken substantially along line 5—5 in FIG. 4 illustrating the tubing in its occluded condition.
Figure 6:
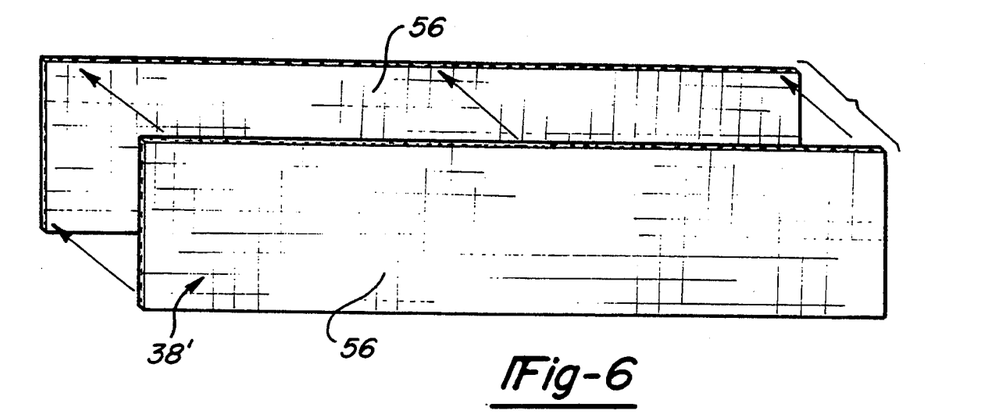
FIG. 6 is an exploded view of a second embodiment of the tubing utilized in the present invention which features two sheets of material being bonded together along their longitudinal edges.
Figure 7:
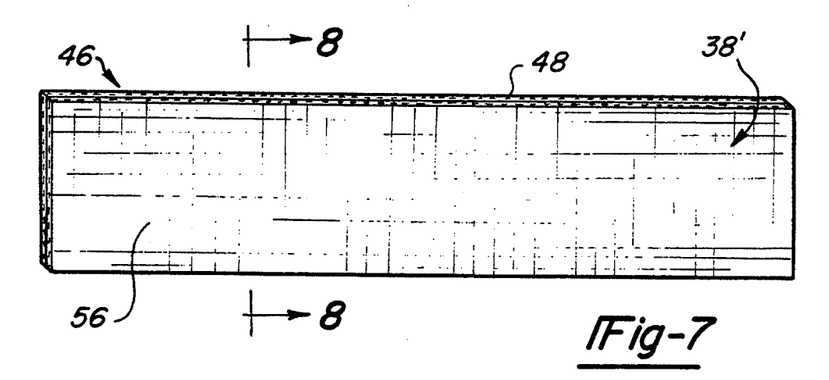
FIG. 7 is a perspective view of a second embodiment of the tubing.
Figure 8:
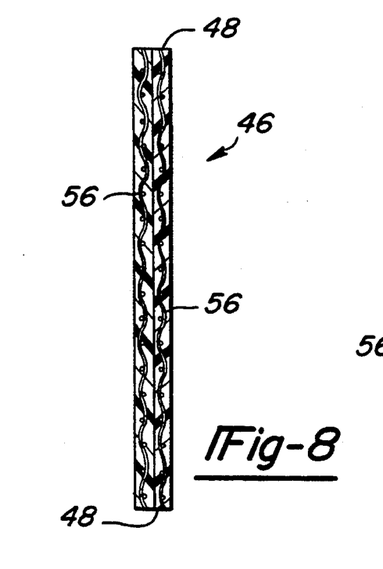
FIG. 8 is a cross-sectional view taken substantially along line 8—8 in FIG. 7 of the tubing in its occluded condition.
Figure 9:
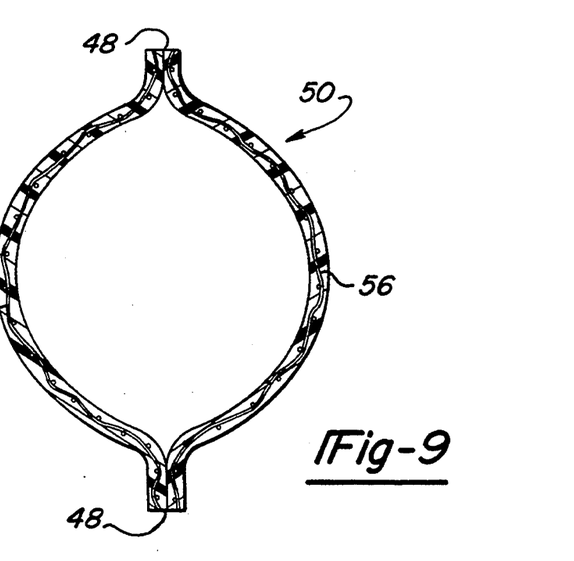
FIG. 9 is a cross-sectional view illustrating the second embodiment of the tubing in its inflated condition.

When the pump 20 is to be operated so that no negative pressures are produced within the tubing 38, the pressure within the vacuum housing 100 is vented to the atmosphere and provided at ambient. As seen in FIGS. 4 and 5, the tubing 38 is naturally flat when no blood is being supplied to the pump 20 and when the external pressure and the pressure within the pumping chamber are equal to ambient. The naturally flat shape of the flexible tube 38 is hereinafter referred to as the "free" condition and is generally designated at 46. The flexible tubing 38 is positioned around the rollers 36 in a manner which places the flat sides 47, exhibited by the tubing 38 in its free condition 46, in surface to surface contact with the circumferential surface of the rollers 36. Thus, the edges 48 of the tubing 38, in its free condition 46, are longitudinally spaced along the rotational axes of the rollers 36.

As the rotor 24 rotates the rollers 36, a peristaltic movement is imparted to the flexible tubing 38. As blood is provided to the inlet end 42 of the flexible tubing 38 at a pressure above ambient, the tubing 38 inflates to the shape generally shown in FIG. 3. This condition is hereafter referred to as inflated condition 50.

Figure 3:
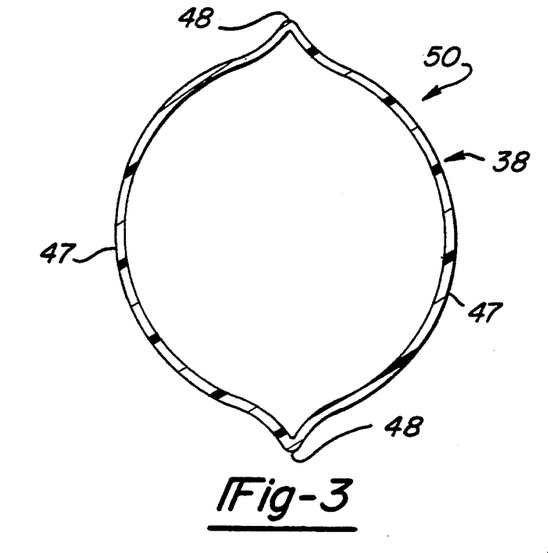
FIG. 3 is a cross-sectional view taken substantially along line 3—3 in FIG. 1 illustrating the tubing in its unoccluded condition.

Blood is received into the inlet end 42, as shown by arrow 52, from a supply tube 53 and driven through the passageway of the flexible tubing 38 until being discharged, as shown by arrow 54, from the outlet end 44 to an outlet tube 55 which may route the blood to an extracorporeal device. If the supply of blood to the pump 20 is discontinued, the blood contained within the flexible tubing 38 will be pumped out by the rollers 36 and the flexible tubing 38 will collapse into its completely occluded free condition 46. Since the flexible tubing 38 is naturally flat, the tubing exhibits no tendency to return to the inflated condition 50 and no negative pressures are generated therein.

In its inflated condition 50, the tubing 38 exhibits what may be referred to as lemon shape. The sides 47 of the inflated tubing 38 are bellowed outward from the increased internal pressure and converge at outwardly directed edges 48. Where the sides 47 converge into the edges 48, the inner radius of curvature exhibited by the tubing approaches zero. Several methods of construction can be utilized to produce tubing 38 having this desired characteristic.

In one method of construction, a thin walled tubing of flexible material, such as vinyl, is heat treated and permanently deformed into the free condition 46 shape. A tubing constructed by this method is illustrated in the cross-sectional views of FIG. 3 and FIG. 5.

A second method of constructing the flexible tubing 38 utilized with the present invention involves adhering two films or sheets of flat, flexible material together along their longitudinal edges to produce a flexible tubing 38 having the desired free condition 46 shape. The edges of the sheets may be adhered by heat sealing or by the use of adhesives. The cross-sectional area of the passageway through the flexible tubing 38 may be constant or may be varied by sealing the edges in a converging or diverging fashion. The latter method resulting in a reduction in the total priming volume required by the pumping chamber.

A peristaltic pump 20 having a tubing 38 with a variable cross-sectional width is shown in FIGS. 11–14. The variable cross-sectional width is directly related to the variable cross-sectional area of the passageway through the tubing 38. As seen in FIGS. 11–14, the illustrated embodiment of the variable cross-sectional tubing 38 is sealed along its edges 46 and includes an inlet or filling region 118 which smoothly increases in cross-sectional width. Since the rotation of the rotor 24 is constant, the volume of the filing region 118 will determine the flow rate for the pump 20. In other words, the fluid volume which enters the filling region 118 and which is trapped between two rollers 36 is the volume of fluid that will be pumped. At the end of the filling region 118 is a constant width intermediate section 119. Approximately at its midsection, the tubing 38 exhibits a smooth width decrease or contraction 120 from the constant width intermediate section 119 until reaching a decreased or narrower constant width section 121 that forms an outlet region 122 for the tubing 38. The width and volume of the outlet region 122 need not be as large as the filling region 118 since it contributes only to flow rate of the fluid and not to pumping volume. By decreasing the width of the tubing in the outlet region 122, the total pump priming volume is reduced.

Another advantage of the reduced width of the tubing 38 is that higher pressures can be withheld, at the locations of the rollers 36, for a given tension in the tubing 38. For example, to maintain a given pressure at the roller 36 locations, a higher tension is required for a wide tubing than for a narrower one.

The equation that governs the stresses in a "thin walled pressure vessel" is $T/2 = P\ R\ W$, where $T/2$ is the total tension of the pump chamber on the outer wall ($\approx \frac{1}{2}$ total tension), P is the pressure in the pump chamber at the roller locations, R is the radius of curvature of the chamber wall at the roller location, and W is the width of the pump chamber at the roller location. During total occlusion, the chamber will be closed or flat and the radius of curvature will approximately equal the radius of curvature of the rollers. Therefore, if W is increased, more tension will be required to maintain the same pressure.

It is especially useful to maintain a narrow outlet region 122 since larger pressures need to be maintained therein. Also, it is advantageous to maintain a relatively narrow cross-section at the beginning of the inlet region 118, where the incoming roller just begins to trap the fluid in the filling region, thus allowing for a lower tension to occlude and hold the filling pressures. Otherwise, more fluid may "slip" past the rollers and not be pumped forward. For this reason, the filling region 118 is not made as wide as the widest part of the tubing 38.

Smoothly varying the cross-section also enhances fluid dynamics in the system by eliminating sudden expansions or contractions which would induce flow separation, backflow, and vortex formation, all of which contribute to pressure loss. The advantages of a variable cross-section pump chamber apply not only to flat tubing, but also to "round" tubing as well.

Generally, the cross-sectional shape of the flexible tubing, and specifically the interior radius of curvature of the edges 48 which approaches zero, reduces the bending stresses applied to the tubing 38 during collapsing of the inflated tubing 38 as caused by the rollers 36 or a reduced inlet pressure. With bending stresses reduced, tubing wear and fatigue is minimized.

As can be seen from the above discussion, tubing 38 must be flexible. However, depending on the actual material used, the material itself may require that the tubing be elastic or inelastic. For example, when silicone (an elastic material) is used as the tubing material, the resiliency of the tubing 38 will allow it to stretch and return to its original length in response to the action of the rollers 36. Silicone, unfortunately, is known to exhibit less than ideal wear characteristics. In another example, when vinyl, exhibiting improved wear characteristics over silicone, is used as the tubing material, once stretched by the action of the rollers 36 it remains stretched.

Fortunately, with the present invention the tubing 38 need not be elastic. A substantially inelastic flexible tubing, hereinafter designated by reference number 38', is illustrated in FIGS. 6 through 9. Generally, the inelastic tubing 38' includes a reinforcement structure which provides those structural attributes which resist stretching. In producing the inelastic tubing 38', a mesh reinforcement 56 which does not substantially elongate under tension is embedded within the sheets of flexible material. The mesh reinforcement 56 may be formed of polyester or a similar material. Since the mesh 56 resists elongation, it prevents substantial longitudinal elongation and lateral contraction in the tubing 38' as a result of tension caused by the rollers 36. As can be seen from the above discussion, vinyl can be used as the tubing 38' material since the vinyl will no longer experience permanent elongation.

The pressure generated within the pumping chamber itself is controlled by the tension of the tubing 38 around the rollers 36. At higher tension, the tubing 38 becomes increasingly occluded at the locations where engaged by the rollers 36, resulting in a higher pressure being held in the pumping chamber. The tension of the tubing 38 is varied by adjusting the positions of the inlet and outlet ends 42 and 44 of the tubing 38 relative to the rotor 24. In achieving this adjustment, a single element is coupled to both ends 42 and 44 of the tubing 38 so as to provide for concurrent and simultaneous adjustment. With a tensioning mechanism of this type, the tension of the flexible tubing 38 and the pressure exhibited by the pumping chamber may be quickly adjusted through a single, yet simultaneous, movement of both ends 42 and 44. (This movement being half the distance of that required by a tensioning mechanism operable with only one end of a tubing as seen in prior art designs.) Also, to permit use of an inelastic tubing 38', the tensioning mechanism 58 is provided with a means for "absorbing" or countering the displacement of the tubing 38 which will be caused by the rollers 36 changing position during rotation.

Two embodiments of the tensioning mechanism 58 are disclosed herein. One embodiment is illustrated in FIGS. 1, 2, and 4 while another embodiment is generally illustrated in FIG. 10.

In both embodiments, the attachment means 40, typically a clamp or other well known mechanism, is coupled to a tension plate 60 to secure the ends 42 and 44 of the tubing 38. The attachment means 40 itself cooperates with the tension plate 60 in a V-shaped portion 62, centrally formed therein and directly toward the rotor 24, such that the ends 42 and 44 of the tubing 38 are secured on opposing legs of the V-shaped portion 62. In using the V-shaped portion 62, the stretch or displacement experienced by the tubing 38, because of the rotation of the rollers 36, is reduced. The V-shaped portion 62 brings the ends 42 and 44 of tubing 38 closer together allowing the tubing 38 to be more fully wrapped around the rollers 36 while allowing the ends 42 and 44 to be mounted perpendicularly to the attachment means 40 and the tension plate 60.

Figure 2:
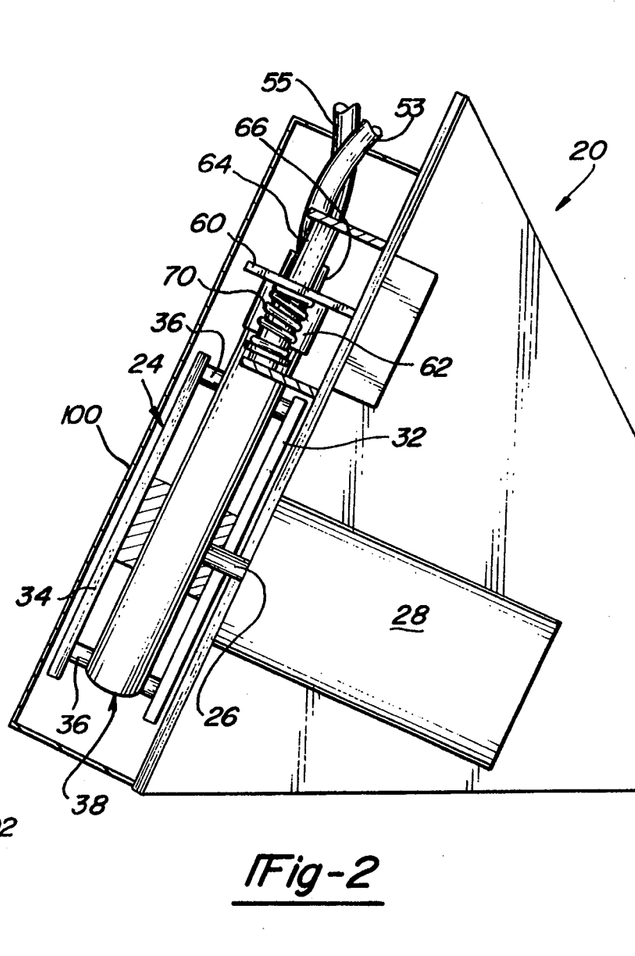
FIG. 2 is a side elevation view of the peristaltic pump illustrated in FIG. 1.

Referring now to the embodiment of the tension mechanism 58 illustrated in FIGS. 1, 2 and 4, the tension plate 60 is supported between two parallel shafts 64 and is mounted for movement relative to the shafts 64. As such, the tension plate 60 is provided with bearings 66, e.g. roller bearings, which allow for a sliding of the tension plate 60 along the shafts 64. Screws 68 are threadably mounted into bores (not shown) of the shafts 64. A spring or biasing member 70 is positioned between the tension plate 60 and operable portion of screw 68 and supports the tension plate 60 thereon. By working the screws 68 into the shafts 64, the spring 70 will be raised or lowered causing the tension plate 60 to move relative to the shaft 64 and thereby adjusting the tension of the tubing 38 around the rollers 36. Also, as the rotor 24 is rotated, the springs 70 will deflect with the tension plate 60 to counter the displacement of the tubing 38.

Figure 10:
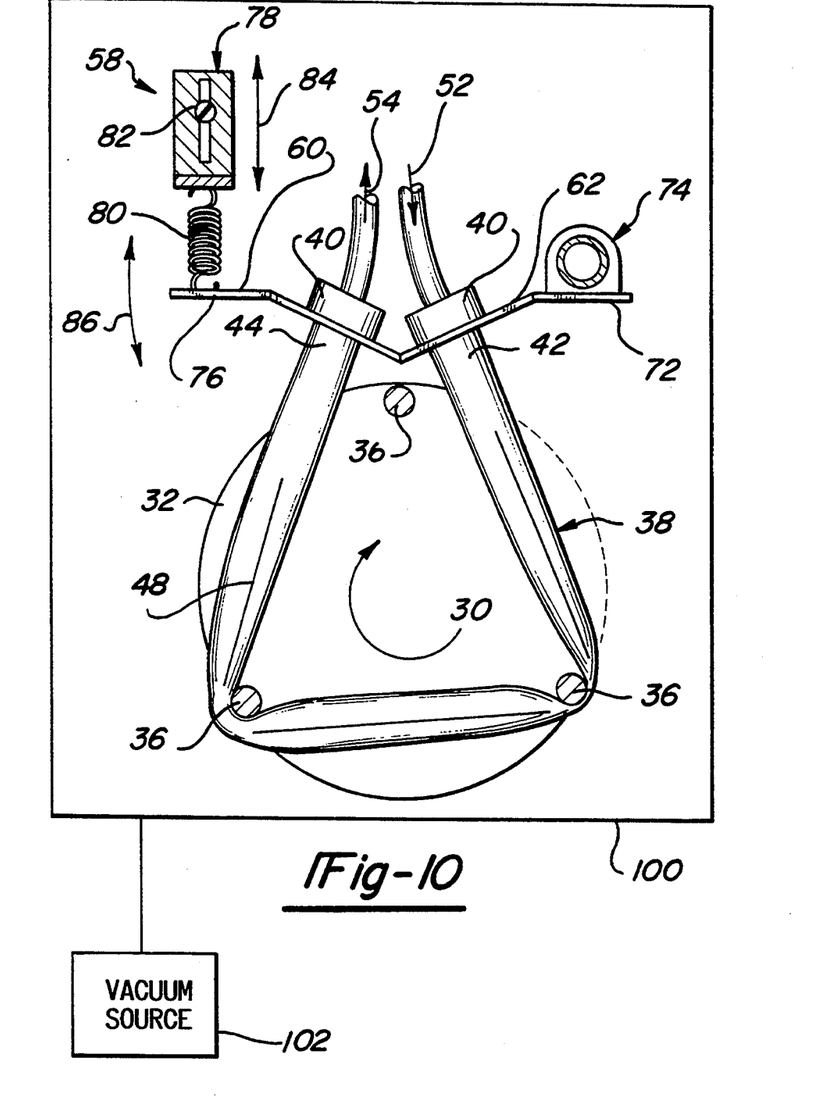
FIG. 10 is a simplified front view of another embodiment of the peristaltic pump of the present invention in which the tension of the tubing is controlled and adjusted through a pivoting mounting plate.
Figure 11:
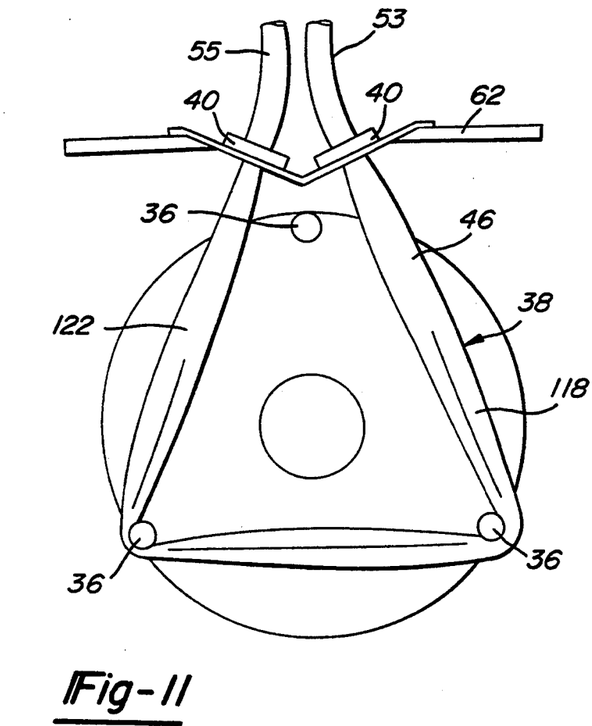
FIG. 11 is a simplified front view of another embodiment of the peristaltic pump of the present invention where the tubing exhibits a variable cross-sectional width.
Figure 12:
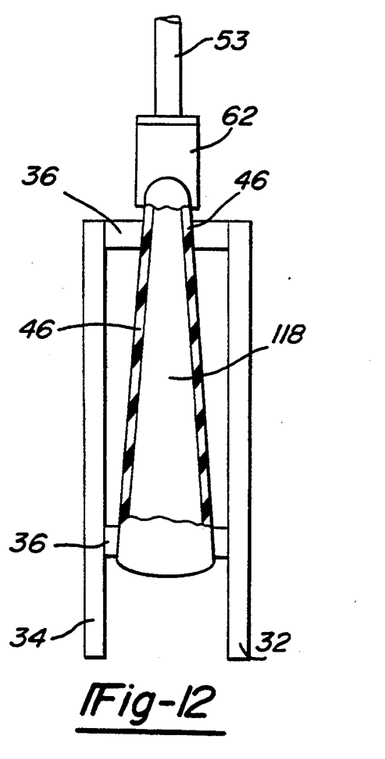
FIG. 12 is a side elevational view of the peristaltic pump shown in FIG. 11.
Figure 13:
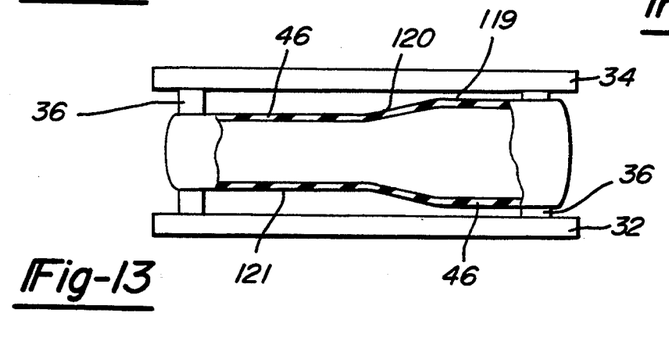
FIG. 13 is a bottom view of the peristaltic pump seen in FIG. 11.
Figure 14:
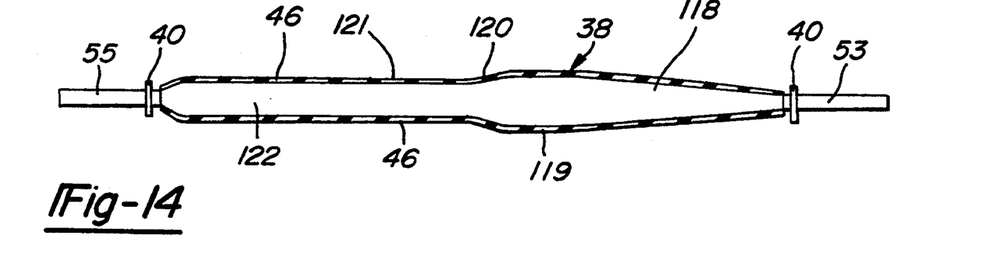
FIG. 14 is a plan view of one embodiment of a tubing having a variable cross-sectional width as used in the peristaltic pump shown in FIG. 11.

In the second embodiment of the tension mechanism 38, generally illustrated in FIG. 10, the tension plate 60 is mounted at one end 72 to the frame 22 of the pump 20 through a pivotable mounting 74. The opposing or free end 76 of the tension plate 60 is coupled to an adjustment block 78 by a spring or biasing member 80. A slider (not shown), mounted within the adjustment block 78, is connected at one end to the spring 80 and at its opposing end to an adjustment screw 82. By moving the slider vertically within the adjustment block 78, as shown by arrow 84, the free end 76 of the tension plate 60 is generally moved along arrow 86 changing the tension of the tubing 38 over the rollers 36. Similar to that seen in the first embodiment, the spring 80 will permit and counter movement of the tension plate 60 during displacement of the tubing 38 resulting from the change in position of the rollers 36 as they are rotated.

When the pump 20 is to be operated as a suction pump, the vacuum source 102 is operated to apply a vacuum and produce a partial vacuum within the housing 100 exteriorly about the tubing 38. With the vacuum applied to the housing 100, the tubing 38 will be induced to form its inflated configuration. This, in combination with the action of the rollers 36, produces a negative pressure in the tubing 38 allowing blood or other body fluids to be "sucked up" by the supply tube 53 and expelled through the outlet tube 55, both of which extend through the housing 100. The amount of suction produced will be equal to the applied vacuum. The vacuum will not affect the outlet end 44 of the tubing 38 because this end of the tubing is always maintained in its "inflated" condition due to the positive pressures generated within.

As an alternative to using a vacuum housing 100 and the tubing 38 exhibiting a completely occluded free condition, a slight and controllable suction can be generated within the tubing 38 by providing a tubing 38, made of a resilient material, with a mildly biased unoccluded free condition having the shape generally shown in FIG. 3. In this embodiment, the tubing 38 is only slightly predisposed into the "inflated" free condition. One way of manufacturing is provided by forming the occluded tubing 38 above, pressurizing the interior of the tubing 38, heating or curing the tubing 38 in the inflated condition, and cooling the tubing 38. As in the previous embodiments of the tubing 38, the radius of curvature at its edges 48 approaches zero ensuring that the tubing 38 can completely collapse without further developing negative pressures.

The bias is provided in an amount which allows the tubing 38 to completely collapse into its occluded or flat condition once a given negative pressure is reached with the tubing 38. The collapse of the tubing 38 is gauged to prevent hazardously large negative pressures, which could hemolyze the blood, from being generated within the pumping chamber.

An additional feature of the present invention is an adjustable occlusion block 88. The occlusion block 88, generally illustrated in FIG. 1, is positioned adjacent to the outlet end 44 of the flexible tubing 38 and is adjustable there against to allow for greater control in the occlusion of the tubing 38 as the rollers 36 disengage therefrom. The occlusion block 88 is provided with an adjustment mechanism (not shown) of a type well known which permits the block 88 to be moved and fixedly positioned toward or away from the rotor 24. Occlusion of the tubing 38 is assisted by a curved surface or raceway 90 of the occlusion block 88. Preferably, the raceway 90 exhibits a radius of curvature differing from the circular path followed by the rollers 36 so that a more constant degree of occlusion is maintained as the rollers 36 begin disengagement adjacent to the outlet end 44 of the tubing 38.

While the above description constitutes the preferred embodiments of the present invention, it will be appreciated that the invention is susceptible to modification, variation and change without departing from the proper scope and fair meaning of the accompanying claims.

We claim:

1. A peristaltic pump for pumping a fluid comprising:
   a frame;
   a plurality of rollers;
   carrier means for carrying said rollers in spaced apart relation along a predetermined path, said carrier means being mounted to said frame;
   drive means for driving said carrier means and causing said rollers to move along said predetermined path;
   a flexible conduit having a wall, an inlet end, an outlet end and a passageway being defined therethrough, said conduit being mounted about said rollers whereby said conduit cooperates along part of its length with said rollers without use of a stator to thereby transmit fluid through said conduit by peristaltic movement; and
   vacuum means for creating at least a partial vacuum exteriorly about the entire length of said conduit which during operation of said peristaltic pump induces negative pressures within said conduit capable of drawing fluid into said conduit through said inlet end and allowing said peristaltic pump to operate as a suction pump, said vacuum means including a housing forming an air-tight enclosure enclosing said conduit therein, said housing also protectively enclosing said rollers and said carrier means.

2. A peristaltic pump as set forth in claim 1 wherein said housing is coupled to a vacuum source for creating said partial vacuum within said housing exteriorly about said conduit.

3. A peristaltic pump as set forth in claim 1 wherein said housing includes means for providing access to said tubing.

4. A peristaltic pump as set forth in claim 1 wherein said conduit is occluded in a free condition when pressure in said passageway is equal to pressure acting on the outside of said wall.

5. A peristaltic pump as set forth in claim 1 wherein said conduit is elastic.

6. A peristaltic suction pump as set forth in claim 1 wherein said conduit is inelastic.

7. A peristaltic pump as set forth in claim 1 wherein said vacuum means creates a partial uniform vacuum exteriorly about the entire length of said conduit.

8. A peristaltic suction pump for pumping a fluid comprising:
   a frame;
   a rotor supported on said frame for rotation about a first axis, said rotor including a plurality of rotatable rollers being mounted radially from said first axis and being carried by said rotor in a generally predetermined path about said first axis;
   drive means being coupled to said rotor for driving said rotor; and
   a flexible resilient tubing having a wall, an inlet end, an outlet end and a passageway defined therethrough for transmitting a fluid, said tubing being positioned about said rollers and being mildly biased so that said passageway is unoccluded in a free condition when pressure in said passageway is generally equal to pressure acting on the outside of said wall, said tubing cooperating along a part of its length with said rollers whereby said rollers at least partially collapse said tubing without the use of a stator generating a negative pressure internally thereof and creating a suction of said fluid into said tubing and through said pump, said tubing being mildly biased so as to collapse into an occluded condition upon generation of a predetermined negative pressure within said passageway to prevent further development of negative pressures in said passageway which are hazardous to said fluid, said tubing including portions generally defining edges, said tubing exhibiting an internal radius of curvature approaching zero at said edges in said free condition, said tubing exhibiting an internal radius of curvature approaching zero at said edges when in said occluded condition.

9. A peristaltic suction pump as set forth in claim 8 wherein said tubing in said occluded condition is fully occluded.

10. A peristaltic pump for pumping a fluid comprising:
   a frame;
   a rotor supported on said frame for rotation about a first axis, said rotor including a plurality of rotatable rollers being mounted radially from said first axis and being carried by said rotor in a generally predetermined path about said first axis;
   drive means being coupled to said rotor for driving said rotor;
   a flexible resilient tubing having a wall, an inlet end, an outlet end and a passageway defined therethrough for transmitting a fluid, said tubing being positioned about said rollers and being mildly biased so that said passageway is unoccluded in a free condition when pressure in said passageway is generally equal to pressure acting on the outside of said wall, said tubing cooperating along a part of its length with said rollers whereby said rollers at least partially collapse said tubing generating a negative pressure internally thereof and creating a suction of said fluid into said tubing and through said pump, said tubing being mildly biased so as to collapse into an occluded condition upon generation of a predetermined negative pressure in said passageway to prevent further development of negative pressures in said passageway which are hazardous to said fluid, said tubing including portions generally defining edges and said tubing exhibiting an internal radius of curvature approaching zero at said edges when in said free condition, said tubing exhibiting an internal radius of curvature approaching zero at said edges when in said occluded condition; and vacuum means for creating at least a partial vacuum exteriorly about the entire length of said tubing which during operation of said peristaltic pump induces negative pressures within said tubing capable of drawing fluid into said tubing through said inlet end thereby allowing said peristaltic pump to operate as a suction pump, said vacuum means including a housing forming an air-tight enclosure enclosing said tubing therein, said housing also protectively enclosing said rollers and said rotor.

11. A peristaltic pump as set forth in claim 10 wherein said housing is coupled to a vacuum source for creating said partial vacuum within said housing exteriorly about said conduit.

12. A peristaltic pump as set forth in claim 10 wherein said housing includes means for providing access to said tubing.

13. A peristaltic pump as set forth in claim 10 wherein said tubing is elastic.

14. A peristaltic pump as set forth in claim 10 wherein said tubing is inelastic.

15. A peristaltic pump as set forth in claim 10 wherein said tubing in said occluded condition is fully occluded.

16. A peristaltic pump as set forth in claim 10 wherein said vacuum means creates a partial uniform vacuum exteriorly about the entire length of said conduit.

* * * * *

UNITED STATES PATENT AND TRADEMARK OFFICE
CERTIFICATE OF CORRECTION

PATENT NO. : 5,342,182
DATED : August 30, 1994
INVENTOR(S) : Jean P. Montoya et al.

It is certified that error appears in the above-indentified patent and that said Letters Patent is hereby corrected as shown below:

Column 10, Line 49, Claim 6 after "peristaltic" delete "suction".

Signed and Sealed this

Sixth Day of December, 1994

Attest:

BRUCE LEHMAN

Attesting Officer     Commissioner of Patents and Trademarks